United States Patent [19]

Miles

[11] Patent Number: 5,353,788
[45] Date of Patent: Oct. 11, 1994

[54] CARDIO-RESPIRATORY CONTROL AND MONITORING SYSTEM FOR DETERMINING CPAP PRESSURE FOR APNEA TREATMENT

[76] Inventor: Laughton E. Miles, 1335 Alma St., Palo Alto, Calif. 94301

[21] Appl. No.: 948,170

[22] Filed: Sep. 21, 1992

[51] Int. Cl.$^5$ .......................... A61M 16/00; A61B 5/08
[52] U.S. Cl. ........................... 128/204.23; 128/204.26; 128/204.21
[58] Field of Search ....................... 128/205.24, 204.18, 128/204.21, 204.23, 719, 204.26, 200.24

[56] References Cited

U.S. PATENT DOCUMENTS

| | | | |
|---|---|---|---|
| 4,655,213 | 4/1987 | Rapaport et al. | 128/205.25 |
| 4,686,975 | 8/1987 | Naimon et al. | 128/204.23 |
| 4,807,616 | 2/1989 | Adahan | 128/204.21 |
| 4,938,212 | 7/1990 | Snook | 128/205.24 |
| 4,944,310 | 7/1990 | Sullivan | 128/848 |
| 4,957,107 | 9/1990 | Sipin | 128/204.18 |
| 5,042,478 | 8/1991 | Kopala et al. | 128/207.18 |
| 5,047,930 | 9/1991 | Martens | 364/413.04 |
| 5,065,756 | 11/1991 | Rapaport | 128/204.18 |
| 5,109,839 | 5/1992 | Blasdell et al. | 128/203.17 |
| 5,117,819 | 6/1992 | Servidio et al. | 128/204.18 |
| 5,134,995 | 8/1992 | Gruenke et al. | 128/204.23 |
| 5,146,918 | 9/1992 | Kallok | 128/419 G |
| 5,148,802 | 9/1992 | Sanders et al. | 128/204.18 |

FOREIGN PATENT DOCUMENTS 8605965 10/1986 PCT Int'l Appl. ................. 128/716

OTHER PUBLICATIONS

Mark H. Sanders et al. Obstructive Sleep Apnea Treated by Independently Adjusted Insoiratory and Expiratory Positive Airway Pressure via Nasal Mask; Chest, vol. 98, pp. 317–324 Aug. 1990.

M. C. Demirozu et al. A Comparison of Nine Nasal Continuous Positive Airway Pressure Machines in Maintaining Mask Pressure During Simulated Inspiration; Sleep, vol. 14, No. 3, pp. 259–262 1991.

Richard P. Millman et al. A Home Monitoring System for Nasal CPAP, Cest, vol. 93, pp. 730–733 Apr. 1988.

Charles G. Alex Effects of continuous positive airway pressure on upper airway and respiratory muscle activity; The American Physiological Society, 0161-7567/87 1987.

A. K. Mahadevia et al. Effects of Expiratory Positive Airway Pressure on Sleep-induced Respiratory Abnormalities in Patients with Hypersomia–Sleep Apnea Syndrome; AM REV Respir Dis 1983, 128:708–711 1983.

R. Douglas McEvoy et al. Treatment of Obstructive Sleep Apnea Syndrome with Nasal Continuous Positive Airway Pressure; Sleep, vol. 4, No. 4, pp. 313–325 1984.

Mark H. Sanders et al. CPAP Via Nasal Mask: A Treatment For Occlusive Sleep Apnea; Chest, vol. 83, No. 1 pp. 144–145 Jan., 1983.

Yuon G. Dupuis, *Ventilators:Theory and Clinical Application* (Princeton, N.J.:C. V. Mosby Co., 1986), pp. 107–117.

John H. Riggs, *Respiratory Facts* (Philadelphia: F. A. Davis Co., 1989), pp. 30–45.

Diane Blodgett, *Manual of Respiratory care Procedures*, Zd ed. (Philadelphia: J. B. Lippincott Co., 1987), pp. 220–225, 278–281.

Joseph J. Carr, *Biomedical Equipment: Use, Maintenance & Management* (Englewood Cliffs, N.J.: Prentice Hall, 1992), pp. 6–7, 328–329.

Raymond W. Southworth, *Digital Computation & Numerical Methods* (New York: McGraw-Hill, 1965) pp. 6–10.

R. Pollock et al., "Improved Technique for Recording Respiratory Data," *Med & Biol. Eng. & Comput.*, Sep., 1977, vol. 15, pp. 541–547.

*Primary Examiner*—Edgar S. Burr
*Assistant Examiner*—Eric P. Raciti
*Attorney, Agent, or Firm*—Paul F. Schenck

[57] ABSTRACT

A system and method for controlling and monitoring externally administered breathing air pressure in a series of cycles. During each cycle, the breathing air pressure starts at a base value and is slowly and progressively increased then rapidly reduced to the base value. If the control and monitoring system detects changes consistent with the presence of upper airway obstruction, the values of breathing air pressure for the next cycle are changed to a higher pressure range. A plurality of vital signs may be monitored and included in the breathing air pressure control system. Information obtained during this procedure is subsequently used to determine the most appropriate externally administered breathing airflow pressure for that person.

36 Claims, 4 Drawing Sheets

CARDIO-RESPIRATORY CONTROL AND MONITORING SYSTEM FOR DETERMINING CPAP PRESSURE FOR APNEA TREATMENT

BACKGROUND OF THE INVENTION

1. Field of the Invention

This invention relates to a medical device and method for automatically determining the correct airflow pressure to be used for the treatment of a serious breathing problem during sleep known as obstructive sleep apnea. It is known that obstructive sleep apnea can be prevented by passing air into the nasal passages at an elevated pressure. This elevated pressure, administered using nasal-continuous-positive-airway-pressure (nasal-CPAP) equipment, prevents the upper airway from collapsing during sleep and therefore prevents the obstructive sleep apnea. In the invention, a microprocessor-controlled all-solid-state physiological monitoring and actuating device, automatically controls and manipulates the airflow pressure administered by the nasal-CPAP equipment while the patient is asleep, while simultaneously measuring and recording a variety of physiological parameters. After the sleep period, the recorded data are analyzed, and the changes in those physiological parameters are related to the airflow pressure. These parameters are measured while the nasal CPAP pressure is below, at, and above, the optimum value for preventing the obstructive sleep apnea. In this way, it is possible to determine the effect of the various airflow pressure levels on the obstructive sleep apnea, and to select the optimum nasal-CPAP airflow pressure for that patient.

Previous methods for determining the correct airflow pressure involved continuous supervision and observation of the patient, with the airflow pressure being manually increased until no further breathing abnormalities or evidence of upper airway resistance are observed. Many different devices can monitor vital signs and correlate the recorded data with the patient's respiratory function. Some devices have the capability of modifying the patient's breathing. However, no other devices automatically control the pressure of the inspired or expired air, and change that pressure in response to the measured vital signs in order to determine the optimum airflow pressure to be used in a therapeutic device.

2. Description of Sleep Apnea

Sleep apnea syndrome is an often serious breathing disorder during sleep characterized by repeated episodes of apnea (cessation of breathing) typically lasting 20–60 seconds in duration. The disorder is often associated with hypoxemia, cardiac arrhythmias, hypertension, disturbed nocturnal sleep, and symptoms such as excessive daytime sleepiness and cognitive impairment. The most common form of sleep apnea is associated with a collapse of the upper airway in the hypopharynx or posterior oropharynx, causing a partial or complete obstruction to the passage of air. After the airway becomes obstructed, it is common for the patient to make little or no effort to breathe, but eventually the patient makes increasing efforts to inspire and expire with excessive fluctuations in intrathoracic pressure. Nevertheless, the obstruction is usually not relieved until the patient has had a brief partial arousal from sleep.

DESCRIPTION OF PRIOR ART

Treatments for Sleep Apnea

Many alternative methods have been devised for treating obstructive sleep apnea. Medication is usually ineffective, but weight loss and avoidance of central nervous depressants such as sleeping pills and alcohol can be helpful, as can treatment of any nasal obstruction or tonsil and/or adenoidal enlargement. Other more specialized surgical procedures such as uvulopalatopharyngoplasty and maxillomandibular surgery have been used with variable success, however the obstruction can be effectively bypassed by chronic tracheostomy. Rarely, treatment of conditions such as hypothyroidism or acromegaly can be beneficial.

Mechanical devices such as dental prostheses and tongue-retaining-devices have been used, also with variable success, but the most effective and widely accepted treatment is nasal-continuous-positive-airway-pressure (nasal-CPAP).

Nasal-CPAP Treatment of Sleep Apnea

Nasal-CPAP treatment of obstructive sleep apnea, involves passing an airflow at elevated pressure (typically 5–15 cm of $H_2$) into the nasal passages though a nasal mask.

This nasal continuous positive airway pressure (nasal-CPAP) prevents the occlusion of the upper airway in patients with obstructive sleep apnea by preventing the development of negative pressure. The increased pressure may also act by "splinting" the upper airway.

Nasal CPAP equipment is currently manufactured and marketed by many companies including: Bird Products Corporation, Palm Springs, Calif.; CEFAM, Vandoeuvre-LesNancy, France; Devilbiss, Somerset, Pa.; Healthdyne Technologies, Marietta, Ga.; Lifecare, Lafayette, Colo.; Med Air Technology, Springfield, Mo.; Medical Industries America, Inc., Adel, Iowa; Mountain Medical Equipment, Littleton, Colo.; Puritan Bennett, Lenexa, Kans.; ResCare Inc., Minneapolis, Minn.; Respironics Inc., Monroeville, Pa.; Vacumed, Ventura, Calif. In one varient of this treatment procedure, the pressure is maintained at a different level during inspiration than expiration. The most widely used apparatus of this type is the BIPAP unit manufactured by Respironics Corporation.

Nasal-CPAP Calibration Procedures

In order to treat a patient with nasal-CPAP, it is necessary to carry out a preliminary calibration procedure to determine the mount of air pressure necessary to prevent the airway obstruction in that patient. Publications describing the usual calibration procedure include Kreiger et al. The technique involves continuous supervision and observation of the patient being treated with nasal-CPAP, with the airflow pressure being manually and progressively increased until no further breathing abnormalities or other evidence of upper airway resistance are observed.

Systems for Automatically Controlling the Nasal CPAP Pressure

U.S. Pat. No. 5,117,819 describes a nasal-CPAP device which uses a microprocessor and pressure transducer to increase (ramp) the nasal-CPAP pressure to the required pressure. This ramp function commences when the machine is powered up, or can be initiated by the patient by pressing a button or switch. The rate, duration, and extent of the pressure increase is either programmable or switch settable. This ramp function is used to allow the patient to fall asleep while receiving lower and more easily tolerated airway pressure, whereas the full, clinically-effective pressure is attained after the patient has fallen asleep. This patent does not describe the use of repeated pressure cycles throughout nocturnal sleep for the purpose of automatic nasal-CPAP calibration.

The physiological monitoring and actuating devices HMS-4000 and HMS-5000 available from Vitalog Monitoring Inc., of Redwood City, Calif., are the only commercially available medical devices designed to control nasal CPAP equipment for the purpose of carrying out automatic nasal CPAP calibration procedures.

Needed Improvements In Calibration Procedures for Nasal CPAP Treatment of Obstructive Sleep Apnea Although nasal-continuous positive airway pressure (CPAP) has been recognized as an effective treatment for obstructive sleep apnea since the method was first described by Sullivan et al in 1981, the usual method for determining the correct pressure involves a 1-2 night, continuously-supervised, inpatient polysomnographic procedure for selecting the optimum airway pressure. This procedure tends to be tedious, labor-intensive, expensive, and inaccurate. Furthermore, many patients have disturbed and atypical sleep when first using the CPAP equipment.

The ideal nasal-CPAP calibration procedure would obtain statistically significant amounts of physiological data just below, at, and just above, the optimum pressure setting—and obtain this data in all sleeping positions and sleep states. This would make the information more accurate and reliable. It would be preferable to use as little physiological data as necessary, and collect that data without using invasive sensors. It would also be preferable to incorporate the sensors into the CPAP equipment itself, and thereby avoid the necessity of applying sensors to the patients body. Furthermore, it may well be important to obtain such information at the time of the initial treatment with nasal-CPAP, and then to re-evaluate the patient when they have become habituated to the equipment, and when the nasal-CPAP treatment has returned their physiology to normal. Finally, it would be desirable to obtain this information in the unsupervised home environment rather than in a special facility under continuous direct observation and clinical supervision. This would save money and allow the patient to be evaluated in his usual environment.

It would also be desirable to devise an automatic method for optimizing the inspiratory versus expiratory pressures; and to develop a method for continuous optimization—that is, for continuously adjusting the pressure to the ideal value throughout the months and years that the patient uses the equipment, during short term fluctuations in the severity of the disorder associated with nasal allergies, sleeping position, use of medication or alcohol, and other factors.

SUMMARY OF THE INVENTION

The invention describes a computerized, multichannel, portable physiological monitoring and actuating device which automatically controls the airflow pressure of nasal-CPAP equipment while measuring multiple physiological parameters during sleep. The system of the present invention is programmed to increase the CPAP pressure at regular or irregular intervals up to a predetermined value, and then rapidly decrease the pressure to the initial value. This cycle is repeated throughout the nocturnal or diurnal sleep. If the monitor recognizes a physiological abnormality indicative of obstructive sleep apnea, then the level of the entire pressure cycle (i.e. the minimal and maximal values) is increased. In this way each airflow pressure cycle will obtain a considerable amount of physiological information below, at, and above the most ideal pressure for treating that patient. After the information is recovered from the physiological monitor, the user can select the best airflow pressure with which to treat the patient, by analyzing the physiological changes occurring during the repetitive pressure cycles,

DETAILED DESCRIPTION OF THE INVENTION

The present invention provides an automatic nasal-continuous-positive-airflow pressure (nasal-CPAP) calibration procedure for the treatment of patients suffering from obstructive sleep apnea.

Figure 1:
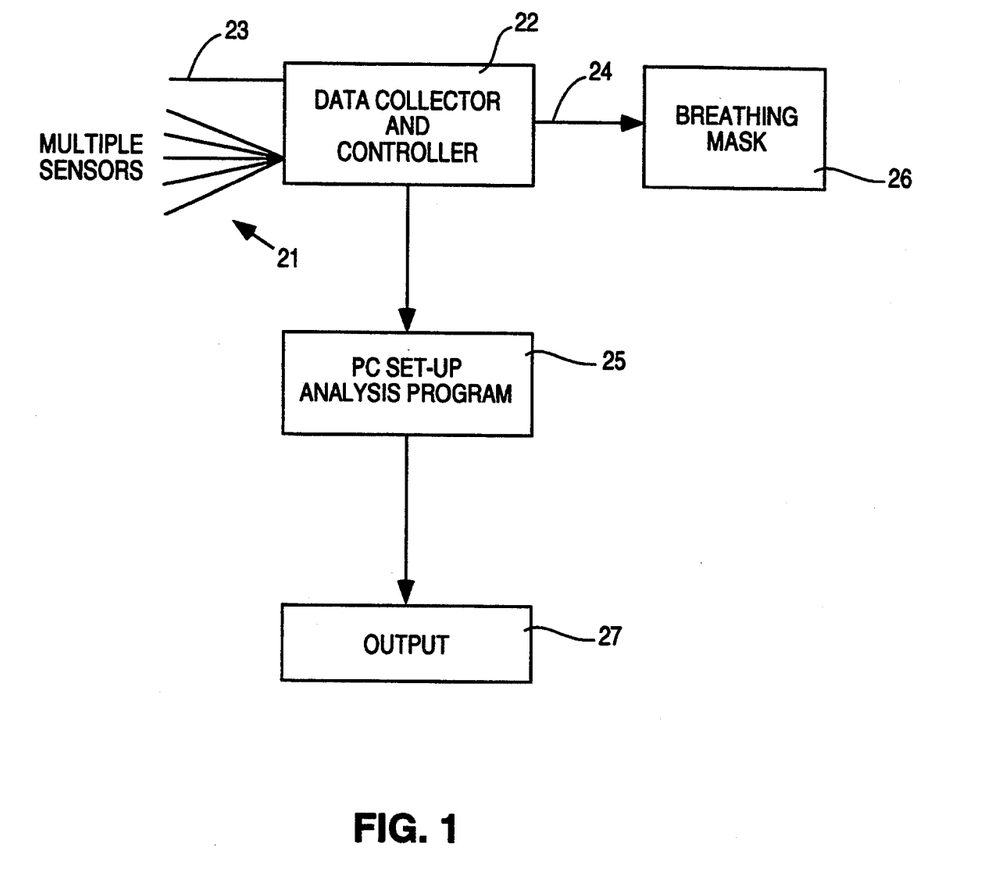
FIG. 1 is a block diagram of the apparatus used to apply the procedure of the present invention.

FIG. 1 is a basic block diagram of the device used to apply the procedure of the present invention. A plurality of sensors 21 are attached to a patient under treatment. The signals monitored include air flow, audio, tidal volume, breathing air pressure, oxygen level, eye movement etc. Data from sensors 21 are collected in physiological monitor and actuating system 22. The monitoring and actuating system 22 includes the basic procedure and control program. Depending on time, entered set-up parameters, and data received via sensors 21, system 22 will issue control signals via outputs 24 to control breathing air pressure at breathing mask 26. Some of sensors 21 may be mounted inside or connected to mask 26. One sensor 23 monitors the blood oxygen saturation level. At the end of a treatment period, system 22 is connected to a processing system 25, such as a personal computer which may provide evaluation results on an output device 27 such as a printer or a visual display. The results of the treatment, including the recorded data and control signals are unloaded onto system 25 for further evaluation. Processing system 25 will prepare the treatment report and may determine the parameters for the next treatment.

Among the vital signs monitored may be chest and abdominal movement, airflow, airflow pressure, breathing sounds, intrathoracic pressure, blood oxygen saturation, heart rate, overall physical movement, leg movement, eye movement, EEG, and sleeping position. All data gathered from the sensors are stored in the Data Collector 22 for later processing by the Analysis Program 25. One or more of the physiological data sensed are used for modifying the airflow pressure cycle. However, it is within the scope of the present invention to use additional or alternative physiological data in order to modify the airflow pressure cycle.

Figure 2:
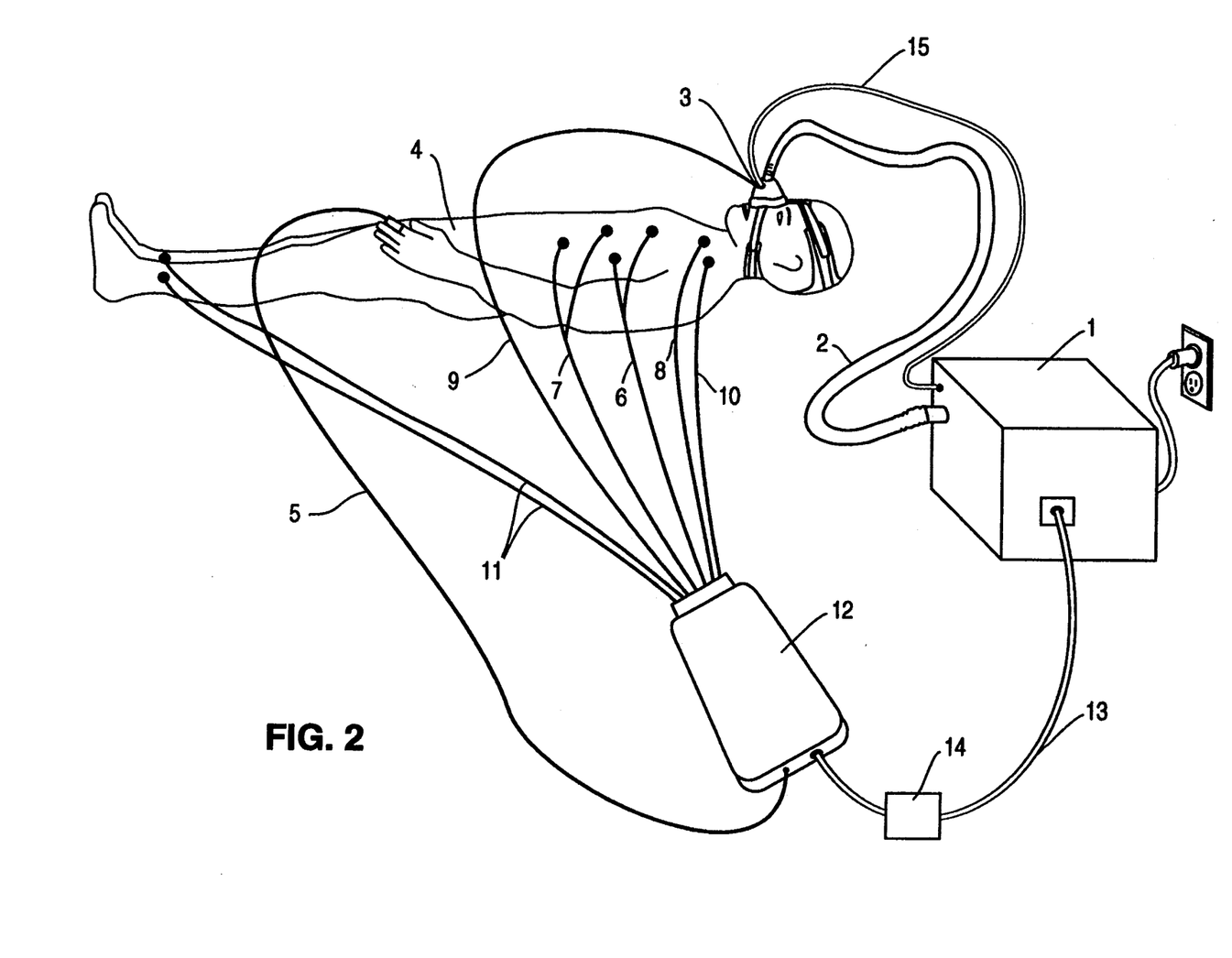
FIG. 2 shows the equipment used in the automatic nasal CPAP calibration procedure.

FIG. 2 shows a typical arrangement of the equipment attached to the patient during this procedure. The nasal- CPAP airflow generator (CPAP device) 1 passes air at elevated pressure into the nasal passages through a large flexible tube 2 and a nasal mask 3. The airflow pressure is measured by using pressure tubing 12 to connect the cavity of the nasal mask 3 to a pressure transducer located in the CPAP device 1. Patient 4 is connected to the physiological monitoring and actuating device HMS-5000 of Vitalog Monitoring Inc. 12 by a series of sensors 5 through 11 including (but not limited to) a pulse oximeter sensor for measuring the oxygen saturation in the blood 5, ECG leads 6, chest and abdominal respiration sensors 7, sleeping position sensor 8, nasal mask thermistor or thermocouple airflow temperature sensors 9, throat microphone 10 and leg movement sensors 11. The physiological monitoring and actuating device is hereafter referred to as PMA-device. The PMA-device 12 is connected to the CPAP device 1 by an electrical cable 13. Through this cable 13 the PMA-device 12 receives (a) outputs from an air pressure transducer in the CPAP device 1, and (b) a quantitative airflow sensor also contained within the CPAP device 1. That airflow sensor measures the amount of air passed into the nasal mask 3 from the CPAP device 1. The pressure transducer measures the air pressure in the nasal mask 3. The cable 13 also contains a control line through which the PMA-device 12 controls the air pressure and airflow produced by the CPAP device 1. The pressure and airflow signals and control line in the cable 13 are passed through a special circuit 14 to electrically isolate the all-battery-powered PMA-device 12 from the 120 VAC powered CPAP device 1. At the end of the procedure, the recorded information is transferred from the PMA-device 12 to a computer. The computer will analyse the data, prepare a report, and help determine the final nasal-CPAP airflow pressure to be used in the long-term treatment of that patient.

Figure 3:
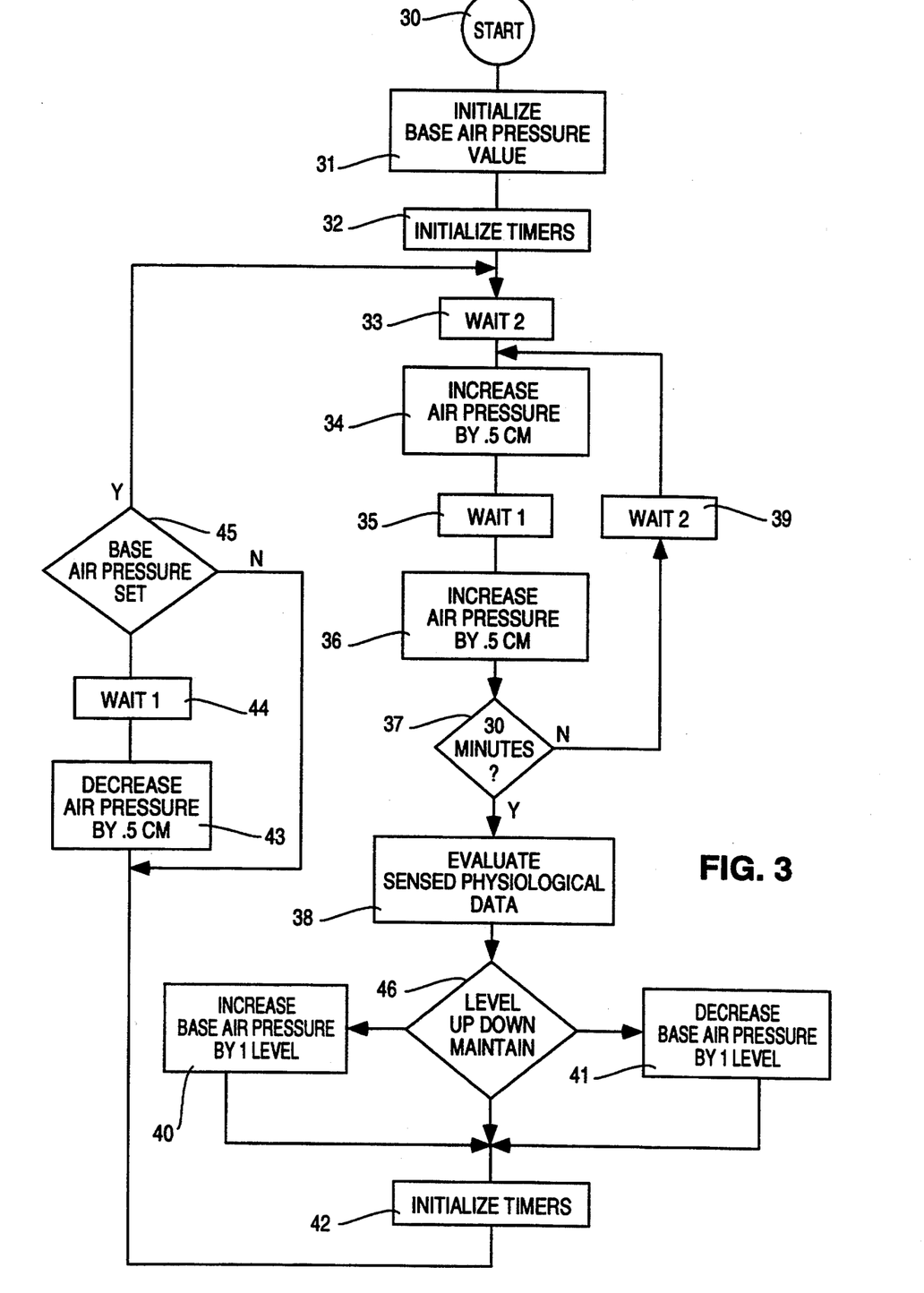
FIG. 3 is a flowchart of the procedure of the present invention.

FIG. 3 shows a schematic flow chart of the operation of the automatic nasal-CPAP monitoring and actuating system. The procedure begins at 30 by establishing the starting base pressure level 31 of the pressure cycle, and by initializing the timing functions 32. Three timers are initiated. A first timer controls the time period for maintaining the airflow pressure at a set value. A second timer allows airflow pressure to be adjusted at 10 second intervals. A third timer allows various physiological parameters to be measured at brief (0.01 to 5.0 second) intervals.

The physiological data is monitored to determine error states. The baseline pressure is regulated following the rules:
Baseline pressure is decreased by 1 cm 41 (but not below the starting baseline pressure) if the physiological data provides no indication of abnormally increased airflow resistance in the upper airway during the previous 2 hours.
The pressure is increased by 1 cm 40 if the physiological data provides an indication of abnormally increased airflow resistance in the upper airway.
As a safety precaution, no pressure adjustments are allowed if the pressure recorded from the nasal mask 3 is not consistent with the pressure specified by the microprocessor of PMA-device 12. Furthermore, an absolute upper limit is placed an the possible airflow pressure.

The operational air pressure is changed in accordance with the following rules: Every 5 minutes within a 30 minute cycle 37 the air pressure is increased by one step (1 cm of water), steps 39, 34, 35, 36 and 37.

If the pressure has reached the maximum value for the present cycle (usually six steps =30 minutes), then in step 38 the system checks whether any of the physiological parameters have provided an indication of abnormally increased resistance to airflow in the upper airway during that 30 minute cycle. For example, in an application using blood oxygen saturation level as a physiological parameter, the system checks whether the blood oxygen level has fallen below a certain level. In step 38, the system decides whether to change the base air pressure level of the pressure cycle 46, makes any necessary baseline value changes 40 or 41, reinitializes the timers 42, and returns the air pressure to the baseline pressure in a plurality of small pressure changes of 0.5 cm 43 in small time intervals 44 of 10 seconds until the set baseline value is reached 45.

Physiological data monitored during the treatment may be used alone or in combination in order to set the base pressure level of the airflow pressure cycle or to change other parameters of the airflow pressure treatment cycle. A high and low limit is established for each of the physiological parameters or combination of parameters used in the control of the airflow pressure treatment. When the physiological parameters are found to be above the high limit or below the low limit, the system acts to change the baseline pressure of the airflow pressure cycle used to treat the obstructive sleep apnea during the automatic nasal CPAP calibration procedure.

Instead of checking physiological data at the end of a full cycle, as shown in FIG. 3 step 38, the decision to change the baseline airflow pressure value can be made inside the control cycle consisting of steps 34, 35, 36, 37 and 39. This allows the system to immediately increase the airflow pressure one step following an abnormal increase in airflow resistance in the upper airway as indicated by a fall in blood oxygen saturation or a predefined change in some other physiological parameter or combination of physiological parameters.

Figure 4:
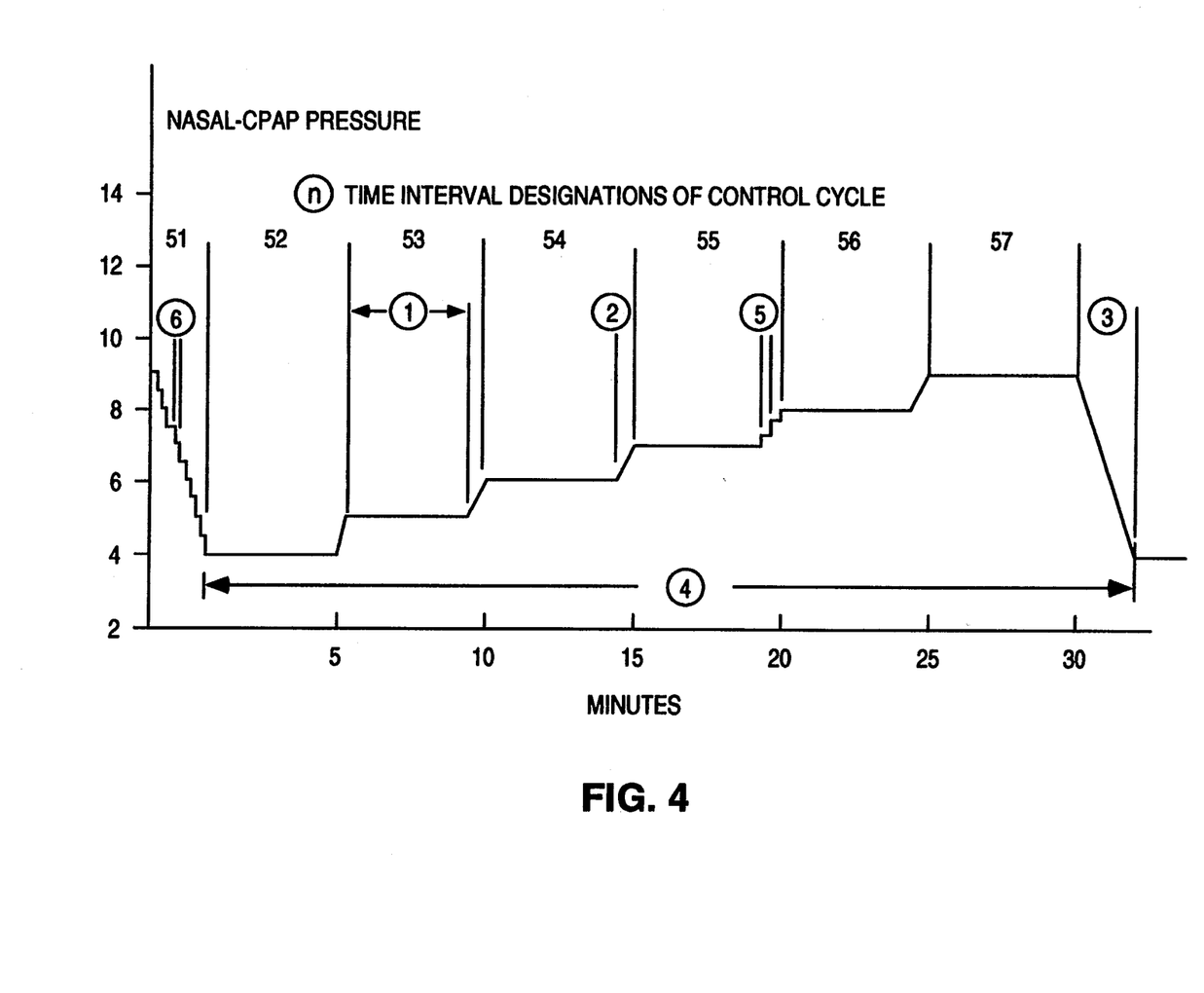
FIG. 4 shows an example of a pressure cycle.

FIG. 4 is an illustration showing the pattern of a typical airflow pressure treatment cycle. The cycle begins by reducing the airflow pressure at a rate of 0.5 cm of $H_2O$ each 10 seconds from a level of 9 cm to the pre-established baseline airflow pressure level of 4 cm, 51. The air pressure remains at this baseline pressure for the remainder of the first 5 minute period 52. The air pressure is then increased in steps of 0.5 cm each 10 seconds to a pressure of 5 cm where it remains for the second 5 minute period 53. In the same way, the pressure in increased at the end of 5 minute period 53, and the following 5 minute periods 54, 55 and 56. At the end of the final 5 minute period 57 the pressure is again reduced to the baseline pressure in 0.5 cm steps every 10 seconds.

This cycle is repeated throughout the diagnostic or therapeutic procedure (usually throughout an overnight recording). Any one or any combination of physiological parameters which can indicate an abnormally increased resistance to airflow in the upper airway of the patient may be used for modifying the airflow pressure cycle. After the diagnostic or therapeutic procedure has been terminated, the user can examine the recorded data in order to determine the ideal air pressure level for subsequent long-term nasal-CPAP treatment of that particular patient.

The description given for the preferred embodiment of the present invention includes a number of parameters which may be changed to adapt the treatment to particular needs and requirements of a certain patient: The rate that the airflow pressure is changed between subsequent 5-minute treatment periods may be increased or decreased; the number of 5-minute treatment periods per major cycle may be increased or decreased; the amplitude of the changes in pressure between each 5-minute treatment period may be increased or increased; and the duration of the 5-minute treatment period may be changed to be shorter or longer than 5 minutes. These changes are within the scope of the present invention and make the same adaptable to the needs of the patient and the desired treatment.

It should be noted however, that for as long as the airflow pressure is elevated above that pressure necessary to abolish the airway obstruction, no airway obstruction will be observed. Therefore in order to more effectively observe and identify the minimum airflow pressure at which the airway obstruction is abolished, it is an essential condition of this invention, that the total duration of time during which the airflow pressure is falling from the highest level of the cycle to the lowest level of the cycle, is much briefer than the total duration of time during which the airflow pressure is increasing from the lowest level of the cycle to the highest level of the cycle.

Two examples of applications of this invention are discussed below. These examples describe the invention as it used in a medical clinic involved in the investigation and treatment of patients with obstructive sleep apnea. These examples are described for purposes of illustration only, and are in no way intended to limit the scope of the present invention.

In both examples, the HMS-4000 or HMS-5000 portable physiological monitoring and actuating system manufactured by Vitalog Monitoring Inc., was used along with the Respironics Inc. BIPAP-STD equipment (set in the CPAP-mode). The all solid-state, battery operated HMS4000 and HMS-5000 monitors record multiple physiological parameters such as EEG, EOG, EMG (chin), ECG waveform, chest and abdominal respiration (inductive plethysmography), nasal/oral airflow using a thermistor or thermocouple, breathing sounds or snoring noise (using a microphone), pulse oximetry, airflow pressure from nasal-CPAP equipment, spirometry airflow from a pneumotachometer or turbine airflow sensor, body movement from a piezo-resistive accelerometer, EMG (legs), sleeping position, body temperature, and electrode impedance, and body, leg, or eye movement using a piezo-ceramic sensor. Digital inputs include an R-wave detector, digital spirometry (turbine airflow sensor) and a patient event marker. The data are recovered from the HMS-4000/5000 by being transferred to an IBM-PC compatible computer though a high speed serial communication link. In addition to recording data, the HMS-4000 and HMS-5000 also controls the nasal-CPAP equipment, using special electrically-isolated circuitry.

The recordings were carried out in unsupervised home environments. The physiological monitors from Vitalog Monitoring Inc. were used to record up to 14 channels of physiological data (including the airflow from the CPAP equipment and the pressure in the CPAP mask) while automatically adjusting the CPAP pressure. The objectives were to obtain statistically significant amounts of physiological data just below, at, and just above, the optimum pressure settings; to obtain this data in all sleeping positions and sleep states; to obtain such information at the time of the initial treatment with nasal-CPAP; and then to re-evaluate the patients when they had become habituated to the equipment and their physiology had returned to normal.

Application One:

In the first application, patients attend a medical clinic during the afternoon to be instructed in the use of the CPAP/BIPAP and equipment from Vitalog Monitoring Inc., and to be fitted with a suitable nasal mask.

The control function is initiated in the clinic when a technician uses the master control panel of the HMS-4000 or HMS-5000 to input a special code. The airflow pressure is initially set at 4 cm $H_2O$, and once the recording is initiated, the monitor increases this pressure by 1 cm each five minutes for 30 minutes before being returned to the baseline level (4 cm) in order to repeat the cycle. When the pressure is changed, the increase or decrease of the pressure occurs at a rate of 0.50 cm of $H_2O$ each 10 seconds. At lights-out (or at any other time), the patient can reset the cycle to begin again at the baseline pressure by pressing a reset button on the control panel. In order to ensure that the pressure cycle covers (brackets) the ideal pressure setting, the location of the cycle is increased by one level whenever there is a genuine fall in oxygen saturation below 85%; and reduced by one level if there has been no change in the location of the cycle for 2 hours. This procedure is referred to as a "type-1" recording. In this way, substantial amounts of data are collected below, at, and above the ideal pressure; in all sleeping positions; and in all sleep states. In this application, level two is omitted so as to maintain a 30 minute cycle while covering a range of 6 cm $H_2O$ pressure, and at the first occurrence of hypoxemia, the cycle changes from 4–10 cm to 5–11 cm pressure.

After the monitor is started up and its function confirmed, the sensors are disconnected, and the patient returns home. At bed-time the patient re-connects the sensors and commences using the CPAP equipment. The information is recovered from the HMS-4000 or HMS-5000 monitor when the patient returns the equipment to the clinic next morning; the recording is reviewed and the CPAP equipment is set to the most appropriate pressure for long-term treatment.

Three to four weeks after this primary calibration procedure, the patient returns for a further CPAP calibration recording, in order to determine whether the selected nasal-CPAP pressure remained optimal after the patient is habituated to the equipment and the treatment has had time to return his physiology to normal. In this "Type 2" recording, the initial baseline pressure is set at three levels below the previously determined optimum pressure.

Application Two

This second automatic nasal-CPAP calibration procedure is similar to the first, except that the only sensor applied directly to the patient's body is a pulse oximetry finger probe. All other sensors (including acoustic, airflow pressure, temperature, movement and absolute airflow (spirometry) are applied directly to the nasal-CPAP equipment itself. This procedure is preferred by most patients over the procedure described in case one, because of the minimal instrumentation.

Selection of Optimal CPAP Pressure

The information recovered from the HMS-4000 or HMS-5000 monitor is evaluated by inspecting the color overview record AND the details of the scored record on a high definition graphic color video display. In addition, the user can inspect the numerical data (e.g. oximetry, breathing abnormalities, airflow, heart rate) broken down by mask pressure and sleeping position. By inspecting the recorded and analysed data in this way, the user can identify the airflow pressures at which the physiological data shows changes consistant with overt obstructive sleep apnea, or changes consistant with abnormally high airflow resistance in the upper airway.

Results

Fifty-five patients (50 males and 5 females) were calibrated as primary procedures, and 40 of these patients (x males y females) were also re-evaluated one month later. The remaining subjects had only secondary (steady-state) recordings. Ages ranged from 25 to 70 years (mean 48.2), and their body weights varied from 125–450 lbs (mean 222 lbs). Most patients were rated as having severe obstructive sleep apnea but severity estimates ranged from mild to severe. The primary studies revealed a mean ideal CPAP pressure of 9 cm±2 cm $H_2O$ during the primary recording (range 7–15), The ideal CPAP pressure selected during the follow-up recording was different by an average of 0.5±1.18 cm $H_2O$ (range −4 to +4). Those showing the greatest falls in ideal pressure had usually lost weight or had undergone some other treatment.

In another study, 20 patients were recorded both with the automatic nasal CPAP procedure and with the usual manual CPAP calibration procedure. The tests were carried out on successive nights in random order. All patients had been previously evaluated by standard diagnostic polysomnography in order to confirm the diagnosis of obstructive sleep apnea and the need for nasal-CPAP treatment. Each record was scored by different investigators blind to each other results. Results showed that there was no statistical difference between the final CPAP pressure determined by the manual method and the automatic procedure. Technician mean CPAP pressure was 9.3±2.2 $H_2O$ versus computer mean pressure of 9.1±2.4 cm $H_2O$. The maximum difference in pressure on any patient was ±1 cm $H_2O$.

What I claim is:

1. A cardio-respiratory apparatus for monitoring physiological signs and controlling breathing air pressure of a person comprising
   monitoring means for gathering one or more types of physiological information from said person;
   means for sensing the pressure of the breathing air being supplied to said person;
   recording means for recording said physiological information and said breathing air pressure;
   base value control means determining a base value for said breathing air pressure based upon said physiological information;
   air supply means for supplying breathing air at determined pressure levels relative to said base value;
   air pressure control means for maintaining said air pressure at one of said pressure levels for a predetermined first time interval, increasing said air pressure at a first predetermined rate during a predetermined second time interval to another one of said pressure levels, repeating said process of maintaining and increasing air pressure for a predetermined number of times, and reducing said air pressure at a predetermined second rate during a predetermined third time interval to said base pressure level,
   said first, second and third time intervals constituting a control cycle of a predetermined fourth time interval; and
   means for repeating said control cycle; wherein said third time interval is at least five times smaller than the sum of said first time intervals plus the sum of said second time intervals.

2. A cardio-respiratory apparatus as claimed in claim 1 wherein said air pressure control means increases said breathing air pressure stepwise during said second time periods for a predetermined number of steps maintaining said breathing air pressure between successive steps for a predetermined fifth time period, and
   returns said breathing air pressure at the end of a control cycle during said third time interval stepwise to said base value, maintaining said breathing air pressure between successive steps for a predetermined sixth time period.

3. A cardio-respiratory apparatus for monitoring physiological signs and controlling breathing air pressure of a person as claimed in claim 1 wherein said monitoring means include
   sensors for collecting physiological signals, physiological data processing means for extracting said types of physiological information from said physiological signals and providing physiological data indicative of an abnormal increase in the airflow resistance in the upper airway of said person using at least one of said physiological signals.

4. A cardio-respiratory apparatus for monitoring physiological signs and controlling breathing air pressure of a person as claimed in claim 2, wherein said monitoring means includes means for setting high and low limit values for each of said types of physiological information used in determining said breathing air pressure base value, at least one of said physiological information when passing said limit values being indicative of an abnormal increase in airflow resistance in the upper airway of said person, and wherein said base value control means increases said base value for a control cycle by a first predetermined value if one or more of said at least one physiological information passes an associated one of said limit values during a preceding one of said control cycles.

5. A cardio-respiratory system for monitoring physiological signs and controlling breathing air pressure of a person as claimed in claim 4, wherein said sensors for collecting physiological signals include sensors for providing a blood oxygen saturation level signal.

6. A cardio-respiratory apparatus for monitoring physiological signs and controlling breathing air pressure of a person as claimed in claim 4, wherein said sensors for collecting physiological signals include sensors for providing a blood oxygen saturation level signal; and wherein
   said base value control means include means for increasing said base value if said blood oxygen saturation level fell below a predetermined value during a predetermined number of said preceding control cycles.

7. A cardio-respiratory apparatus for monitoring physiological signs and controlling breathing air pressure of a person as claimed in claim 3,
   wherein said monitoring means includes means for setting high and low limit values for each of said types of physiological information used in determining said breathing air pressure base value, at least one of said physiological information when passing said limit values being indicative for an abnormal increase in airflow resistance in the upper airway of said person, and wherein said base value for a control cycle is increased by a first predetermined value if one or more of said at least one physiological information passes an associated one of said limit values during a predetermined number of said control cycles, and wherein said air supply means decreases said base value for a control cycle by a second predetermined value if one or more of said at least one physiological information did not pass any associated one of said limit values during said predetermined number of said control cycles.

8. A cardio-respiratory apparatus for monitoring physiological signs and controlling breathing air pressure of a person as claimed in claim 3, wherein said monitoring means includes means for setting high and low limit values for each of said types of physiological information used in determining said breathing air pressure base value, at least one of said physiological information when passing said limit values being indicative of an abnormal increase in the airflow resistance in the upper airways of said person, and wherein said base value control means decreases said base value for a control cycle by a first predetermined value if one or more of said at least one physiological information did not pass any associated one of said limit values during a predetermined number of said control cycles.

9. A cardio-respiratory apparatus for monitoring physiological signs and controlling breathing air pressure of a person as claimed in claim 8 wherein said sensors for collecting physiological signals include sensors for providing a blood oxygen saturation level signal; and wherein said base value control means include means for decreasing said base value if said blood oxygen saturation level did not fall below a predetermined value during a predetermined number of said preceding control cycles.

10. A cardio-respiratory system for monitoring physiological signs and controlling breathing air pressure of a person as claimed in claim 3 wherein said sensors for collecting physiological signals include sensors for providing a blood oxygen saturation level signal.

11. A cardio-respiratory apparatus for monitoring physiological signs and controlling breathing air pressure of a person as claimed in claim 10, wherein said air supply means include base value control means for increasing and decreasing said base value of said air pressure, and wherein said base value control means increases said base value for a control cycle if said blood oxygen saturation level fell below a predetermined value during a preceding one of said control cycles, and wherein said base value control means decreases said base value for said control cycle if said blood oxygen saturation level remained above said predetermined level during a predetermined number of said control cycles.

12. A cardio-respiratory apparatus for monitoring physiological signs and controlling breathing air pressure of a person as claimed in claim 8 wherein said sensors for collecting physiological signals include sensors for providing a blood oxygen saturation level signal; and wherein said base value control means include
means for decreasing said base value if said blood oxygen saturation level did not fall below a predetermined value during a predetermined number of said preceding control cycles, and
means for increasing said base value if said blood oxygen saturation level fell below a predetermined value during a predetermined number of said preceding control cycles.

13. A cardio-respiratory monitoring and control method for monitoring physiological signs and controlling breathing air pressure of a person during repetitive control cycles, each said control cycle comprising the steps of monitoring and recording said physiological signs and said breathing air pressure of said person;

determining a base value for said breathing air pressure based upon said physiological information;

cyclicly supplying breathing air at determined pressure levels relative to said base value, including the steps of:

(a) maintaining said air pressure at one of said pressure levels for a predetermined first time interval, and (b) increasing said air pressure at a predetermined first rate during a predetermined second time interval to another one of said pressure levels, and repeating step (b) a predetermined number of times before reducing said air pressure at a predetermined second rate during a predetermined third time interval to the base pressure value pressure, thereby completing a control cycle of a duration equal to a predetermined fourth time interval; and repeating said control cycle; wherein in each said control cycle the sum of each said first time interval plus the sum of each said second time intervals is at least five times longer than said third time interval.

14. A cardio-respiratory monitoring and control method as claimed in claim 13 wherein said breathing air pressure is cyclicly increased from said base value stepwise in intervals of 5 minutes and returned to said base value at the end of 30 minutes, with all changes in pressure occur at the rate of 0.50 cm $H_2O$ each 10 seconds.

15. A cardio-respiratory monitoring and control method as claimed in claim 13, wherein the increases in air pressure between successive ones of said air pressure levels at said first rate are carried out in substeps each having a predetermined fifth time interval.

16. A cardio-respiratory monitoring and control method as claimed in claim 13, wherein the decrease in air pressure to said base level pressure at said second rate is carried out in substeps each having a predetermined sixth time interval.

17. A cardio-respiratory monitoring and control method as claimed in claim 13 wherein said fourth time interval is about 30 minutes, and includes 6 of said first time intervals in which said breathing air pressure is held at 6 different air pressure levels.

18. A cardio-respiratory monitoring and control method as claimed in claim 13 wherein said first rate is 0.5 $H_2O$ per 10 seconds.

19. A cardio-respiratory monitoring and control method as claimed in claim 13 wherein said base pressure value is 4 cm.

20. A cardio-respiratory monitoring and control method as claimed in claim 13 wherein said base value of said breathing air pressure is maintained for a full control cycle time.

21. A cardio-respiratory monitoring and control method as claimed in claim 13 wherein said breathing air pressure is decreased to said base value and maintained said base value for a full control cycle time.

22. A cardio-respiratory monitoring and control method as claimed in claim 13 wherein said breathing air pressure is cyclicly increased from said base value stepwise in intervals of 5 minutes in two sub-steps in intervals of 10 seconds, and returned to said base value at the end of 30 minutes.

23. A cardio-respiratory monitoring and control method as claimed in claim 13, said method further including processing the data obtained from said monitoring of physiological information,
said processing including determining physiological induced changes in said breathing air pressure, and providing a measure of an abnormal increase in the airflow resistance in the upper airway of said person based on said physiological induced changes.

24. A cardio-respiratory monitoring and control method as claimed in claim 23, said monitoring of physiological information includes the measurement of blood oxygen saturation.

25. A cardio-respiratory monitoring and control method as claimed in claim 23, wherein said method further includes setting high and low limit values for each type of said physiological information and said physiological induced changes in said breathing air pressure, said limit values being indicative of an abnormal increase in the airflow resistance of the upper airway;
said method further includes
repetitive execution of said control cycle, and increasing said base pressure value for a following control cycle by a predetermined value if one or more of said physiological information or physiologically induced changes in said breathing air pressure passes an associated one of said limit values during one of said preceding control cycles.

26. A cardio-respiratory monitoring and control method as claimed in claim 25, said monitoring of physiological information includes the measurement of blood oxygen saturation.

27. A cardio-respiratory monitoring and control method as claimed in claim 23, said method further including processing the data obtained from said monitoring of physiological information,
said processing further including
determining patterns in said physiological information and said physiological induced changes of said breathing air pressure for providing indications of abnormal increase in the airflow resistance in the upper airway of said person based on said physiological induced changes.

28. A cardio-respiratory monitoring and control method as claimed in claim 27, wherein said method further includes setting high and low limit values for said patterns determined in said physiological information and said physiological induced changes in said breathing air pressure, said limit values being indicative of an abnormal increase in the airflow resistance of the upper airway;
said method further includes
repetitive execution of said control cycle, and increasing said base pressure value for a following control cycle by a predetermined value if one or more of said physiological information or physiologically induced changes in said breathing air pressure passes an associated one of said limit values during one of said preceding control cycles.

29. A cardio-respiratory monitoring and control method as claimed in claim 28, said monitoring of physiological information includes the measurement of blood oxygen saturation.

30. A cardio-respiratory monitoring and control method as claimed in claim 23, wherein said method further includes setting high and low limit values for each type of said physiological information and said physiological induced changes in said breathing air pressure, said limit values being indicative of an abnormal increase in the airflow resistance of the upper airway;
said method further includes
repetitive execution of said control cycle, and decreasing said base pressure value for a following control cycle by a predetermined value if none of said physiological information or physiologically induced changes in said breathing air pressure passed an associated one of said limit values during one of said preceding control cycles.

31. A cardio-respiratory monitoring and control method as claimed in claim 30, said monitoring of physiological information includes the measurement of blood oxygen saturation.

32. A cardio-respiratory monitoring and control method as claimed in claim 23, said method further including processing the data obtained from said monitoring of physiological information,
said processing further including
determining patterns in said physiological information and said physiological induced changes of said breathing air pressure for providing indications of abnormal increase in the airflow resistance in the upper airway of said person based on said physiological induced changes.

33. A cardio-respiratory monitoring and control method as claimed in claim 32, wherein said method further includes setting high and low limit values for said patterns determined in said physiological information and said physiological induced changes in said breathing air pressure, said limit values being indicative of an abnormal increase in the airflow resistance of the upper airway;
said method further includes
repetitive execution of said control cycle, and increasing said base pressure value for a following control cycle by a predetermined value if one or more of said physiological information or physiologically induced changes in said breathing air pressure passes an associated one of said limit values during one of said preceding control cycles, and
decreasing said base pressure value for a following control cycle by a predetermined value if none of said physiological information or physiologically induced changes in said breathing air pressure passed an associated one of said limit values during one of said preceding control cycles.

34. A cardio-respiratory monitoring and control method as claimed in claim 33, said monitoring of physiological information includes the measurement of blood oxygen saturation.

35. A cardio-respiratory monitoring and control method as claimed in claim 23, wherein said method further includes setting high and low limit values for each type of said physiological information and said physiological induced changes in said breathing air pressure, said limit values being indicative of an abnormal increase in the airflow resistance of the upper airway;

said method further includes
repetitive execution of said control cycle, and increasing said base pressure value for a following control cycle by a predetermined value if one or more of said physiological information or physiologically induced changes in said breathing air pressure passes an associated one of said limit values during one of said preceding control cycles, and decreasing of said base pressure value for a following control cycle by a predetermined value if none of said physiological information or physiologically induced changes in said breathing air pressure passed an associated one of said limit values during one of said preceding control cycles.

36. A cardio-respiratory monitoring and control method as claimed in claim 35, said monitoring of physiological information includes the measurement of blood oxygen saturation.

* * * * *